United States Patent [19]

Frankel et al.

[11] Patent Number: 4,534,895

[45] Date of Patent: Aug. 13, 1985

[54] 1-AZIDOMETHYL-3,5,7-TRINITRO-1,3,5,7-TETRAZACYCLOOCTANE AND SYNTHESIS THEREOF VIA AZIDATION WITH ACETYL AZIDE

[75] Inventors: Milton B. Frankel, Tarzana; Dean O. Woolery, II, Reseda, both of Calif.

[73] Assignee: Rockwell International Corporation, El Segundo, Calif.

[21] Appl. No.: 534,992

[22] Filed: Sep. 22, 1983

[51] Int. Cl.[3] ............................................. C07D 257/02
[52] U.S. Cl. ...................................... 260/239 BC
[58] Field of Search ...................... 260/239 BC

[56] References Cited

PUBLICATIONS

Zibral et al., Monatsh. Chem. 1969 100(4) pp. 1438–1449.
Chem. Abst. 112865h, vol. 71, (1969), p. 373.

*Primary Examiner*—Glennon H. Hollrah
*Assistant Examiner*—D. B. Springer
*Attorney, Agent, or Firm*—H. Fredrick Hamann; Harry B. Field

[57] ABSTRACT

A method of introducing N-azido alkyls into cyclic nitramines comprises reacting under non-basic conditions in an inert organic solvent a N-halo alkyl cyclic nitramine with the novel azidation agent acetyl azide to form the corresponding N-azido alkyl cyclic nitramine.

9 Claims, No Drawings

1-AZIDOMETHYL-3,5,7-TRINITRO-1,3,5,7-TETRAZACYCLOOCTANE AND SYNTHESIS THEREOF VIA AZIDATION WITH ACETYL AZIDE

STATEMENT OF GOVERNMENT INTEREST

The Government has rights in this invention pursuant to Contract (or Grant) No. F49620-81-C-0031 awarded by the U.S. Department of the Air Force.

BACKGROUND OF THE INVENTION

1. Field of the Invention

This invention relates to energetic azido compounds and, more specifically, to a method for the synthesis of azido compounds under non-basic conditions, using acetyl azide as the azidation agent.

2. Description of the Prior Art

When 1,5-methylene-3,7-dinitro-1,3,5,7-tetrazacyclooctane (compound 1), a compound readily prepared by nitrolysis of hexamethylenetetramine, is treated with an equivalent of 98% nitric acid in excess acetic anhydride, 1-acetoxymethyl-3,5,7-trinitro-1,3,5,7-tetrazacyclooctane (compound 3) is formed. In the reaction, cleavage of the bridge occurs; one of the bridgehead nitrogen atoms acquires a nitro group, the other holds the acetoxymethyl group. The reaction may be considered to involve nitrolysis of (Compound 1) to the methyol derivative (Compound 2), followed by acetylation of the hydroxy group by the acetic anhydride.

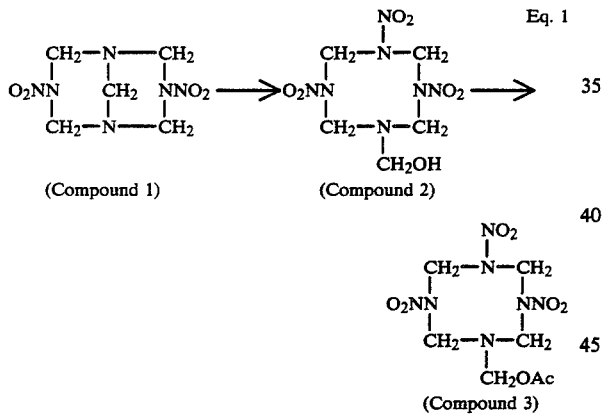

(Compound 1)  (Compound 2)

(Compound 3)

Bell and Dunstan (J.Chem.Soc.(c), 862–869 (1969)) investigated reactions of the six, seven, and eight-membered ring acetates with various nucleophiles such as alcohols and inorganic salts. One aspect of their work was the reactions of these ring acetates with sodium azide, in efforts to prepare the corresponding ring azides. The reaction of (Compound 3) and the six-membered ring acetate with sodium azide in dimethylformamide medium gave primarily decomposition products with a trace of (Compound 1). Only in the case of the seven-membered ring acetate was it possible to obtain the corresponding azido compound.

1-Azidomethyl-3,5,7-trinitro-1,3,5,7-tetracyclooctane (Compound 5) was of particular interest to our continuing studies on the synthesis of energetic azido compounds because of its structural relationship to the well-known high explosive 1,3,5,7-tetranitro-1,3,5,7-tetrazacyclooctane (HMX). Since Bell and Dunstan were unsuccessful in preparing (Compound 5) by the classical method of the treatment of (Compound 3) with sodium azide, other possible synthetic routes were investigated. It was apparent that under the basic conditions of the nucleophilic reaction with sodium azide, decomposition of the eight-membered ring was occurring. Therefore, the present invention concluded that the best chance for success with this reaction would be under nonbasic conditions.

Dunning and Dunning (J.Chem.Soc., 2925(1950)) have reported that treatment of 1-methoxymethyl-3,5-dinitro-1,3,5-triazacyclohexane with acetyl chloride and acetyl bromide gave 1-chloromethyl-3,5-dinitro-1,3,5-triazacyclohexane and 1-bromomethyl-3,5-dinitro-1,3,5-triazacyclohexane, respectively. This chemistry was applied to the current work on the eight-membered ring derivatives. Treatment of (Compound 3) with acetyl bromide gave a quatitative yield of 1-bromomethyl-3,5,7-trinitro-1,3,5,7-tetrazacyclooctane (Compound 4). Attempts to convert Compound 4 to Compound 5 with sodium azide were unsuccessful. Thus, a novel method Eq. 2 was needed and invented for the conversion of Compound 4 to Compound 5.

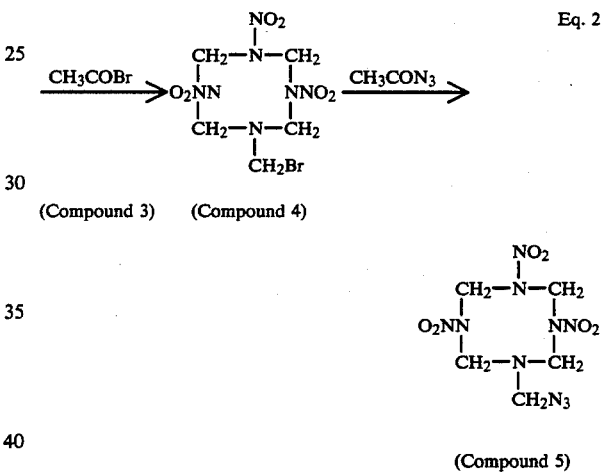

(Compound 3)  (Compound 4)

(Compound 5)

OBJECTS OF THE INVENTION

Accordingly, it is an object of the present invention to provide a new azidation agent, acetyl azide.

Another object of the present invention is to provide a method of making N-azido alkyl cyclic nitramines.

Still another object of the present invention is to provide non-basic means for introducing N-azido alkyls into cyclic nitramines.

Yet a further object of the present invention is to provide a safe method for preparing energetic polynitro compounds of the present invention.

Still a further object of the present invention is to use in-situ generated acetyl azide as the azidation agent for the claimed reaction.

Other objects, advantages and novel features of the present invention will become apparent from the following detailed description of the invention.

SUMMARY OF THE INVENTION

Accordingly, it has been found that acetyl azide is an excellent azidation agent. Thus, the current invention provides a heretofore unobtainable method of introducing N-azido alkyls into cyclic nitramines. The product is obtained by reacting under non-basic conditions a N-halo alkyl cyclic nitramine with a solution of acetyl azide in an inert organic solvent. Specifically, 1-azidomethyl-3,5,7-trinitro-1,3,5,7-tetrazacyclooctane is prepared, at below 40° C. and under non-basic conditions, by reacting a solution of acetyl azide in methylene chloride with 1-bromomethyl-3,5,7-trinitro-1,3,5,7-tetrazacyclooctane. The desired end product is then collected and purified in accordance with standard techniques.

DESCRIPTION OF THE PREFERRED EMBODIMENTS

In accordance with the presently-claimed invention, it has been found that acetyl azide is an excellent azidation agent. This new use of acetyl azide provides a new, efficient and heretofore unobtainable method of generating N-azido alkyl cyclic nitramines by reacting a N-halo alkyl cyclic nitramine with acetyl azide. Reaction conditions for this azidation reaction dictate that the temperature should be maintained under about 40° C., it should be conducted in an inert organic solvent such as methylene chloride, carbon tetrachloride, or chloroform, while keeping the reaction system under non-basic conditions.

Tests conducted with the N-halo alkyl cyclic nitramines indicated that the preferred ring structures were six-, seven-, and eight-membered rings while the most preferred was the eight-membered ring. Further, although any of the halogens would be adequate, those of bromo and chloro are preferred, and the bromo is most preferred.

The azidation reactions with acetyl azide also taught that although the preferred temperature range for the azidation was between 10° and 15° C., that anything below about 40° C., the decomposition temperature of acetyl azide, would be adequate. Further, it was discovered that the in-situ generation of the acetyl azide was simpler and more efficient than attempting to isolate the acetyl azide and then use it in a subsequent reaction.

Specifically, there is presented herein a method of preparing 1-azidomethyl-3,5,7-trinitro-1,3,5,7-tetrazacyclooctane by combining a solution of acetyl chloride in methylene chloride with an aqueous solution of sodium azide to generate a two-phase system wherein the lower layer is acetyl azide in methylene chloride and the upper layer is aqueous by-product. The upper by-product layer may then be removed by any conventional process and 1-bromomethyl-3,5,7-trinitro-1,3,5,7-tetrazacyclooctane is added to the non-basic lower layer of acetyl azide in methylene chloride. The reactants then go through the azidation reaction at preferably between about 10° and about 15° C. to generate the desired product, 1-azidomethyl-3,5,7-trinitro-1,3,5,7-tetrazacyclooctane, in accordance with Equation 2 above. Finally, the product is collected and purified in accordance with standard techniques.

By way of illustration and not limitation, the following experimental information is provided:

CAUTION. The polynitrocompounds described in this invention are explosives and should be handled with due care. In particular, reactions should be run on a small scale behind adequate shielding. Personnel should be equipped with safety glasses and fire-retardant laboratory coats.

Satisfactory analyses were obtained for all elements except oxygen. The melting points are uncorrected. IR spectra were taken with a Perkins Elmer 137 infracord, HPLC analyses were determined with a Waters HPLC unit.

1-Bromomethyl-3,5,7-trinitro-1,3,5,7-tetrazacyclooctane (Compound 4)

Acetyl bromide (500 g, 4.07 mol) was cooled to $-10°$ C. under $N_2$. Compound 3 (98.3 g, 0.304 mol) was added, the mixture was stirred for 0.5 h at 10° C. and filtered under $N_2$. The product, which is hygroscopic, was washed with ether (2×250 mL), and dried in a vacuum oven for 5 h at 40° C. The yield of Compound 4 was 101 g (97%), m.p. 149°–150° C. Analysis calculated for $C_5H_{10}BrN_7O_6$: C, 17.44; H,2.91: Br,23.24; N,28.49. Found: C,17.31; H,3.08; Br,23.13; N,28.43.

1-azidomethyl-3,5,7-trinitro-1,3,5,7-tetrazacyclooctane (Compound 5)

A solution of sodium azide (345 g, 5.45 mole) in water (1200 mL) was cooled to 5° C. and with good stirring a solution of acetyl chloride (286 g, 3.64 mol) in methylene chloride (640 mL) was added in 2.5 h, maintaining the temperature at 5° C. with external cooling. The upper aqueous layer was siphoned off and Compound 4 (101 g, 0.294 mol) was added. The mixture was stirred for 3 h at 10°–15° C. and filtered. The white solid was washed with methylene chloride (2×200 mL), water (200 mL), and ether (2×200 mL), and dried in a vacuum oven overnight at 40° C. The yield of Compound 5 was 71 g (79%), m.p. 130°–131° C. IR (KBr) 2080 $cm^{-1}$ ($N_3$), 1540 $cm^{-1}$ ($N-NO_2$). HPLC analysis showed a single peak. Analysis calculated for $C_5H_{10}N_{10}O_6$: C,19.61: H,3.27; N,45.75. Found: C,19.99: H,3.28; N,44.99.

Obviously, many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A method of preparing 1-azidomethyl-3,5,7-trinitro-1,3,5,7-tetrazacyclooctane, which comprises the steps of:
   combining the reactants 1-bromomethyl-3,5,7-trinitro-1,3,5,7-tetrazacyclooctane with acetyl azide in an inert organic solvent; and
   reacting said reactants under non-basic conditions while maintaining the reaction temperature below about 40° C.

2. The method of claim 1 wherein said acetyl azide is prepared in-situ by reacting acetyl chloride in an inert organic solvent with aqueous sodium azide to form a two-phase system wherein the lower layer is acetyl azide in said inert organic solvent and the upper layer is aqueous by-product, and removing the aqueous by-product layer.

3. The method of claim 2 wherein said combining is effected by adding said 1-bromomethyl-3,5,7-trinitro-1,3,5,7-tetrazacyclooctane to said acetyl azide in said inert organic solvent.

4. The process of claim 3 wherein said process further comprises collecting said purifying said 1-azidomethyl-3,5,7-trinitro-1,3,5,7-tetrazacyclooctane.

5. The method of claim 1 wherein said reaction temperature is between about 10° and about 15° C.

6. The method of claim 1 wherein said inert organic solvent is selected from the group consisting of methylene chloride, carbon tetrachloride, and chloroform.

7. The method of claim 6 wherein said solvent is methylene chloride.

8. A method of preparing 1-azidomethyl-3,5,7-trinitro-1,3,5,7-tetrazacyclooctane, which comprises the steps of:

combining a solution of acetyl chloride in methylene chloride with a solution of sodium azide in water;

reacting said acetyl chloride with said sodium azide to generate a two-phase system wherein the lower layer is acetyl azide in methylene chloride and the upper layer is aqueous by-product;

removing the upper aqueous layer from said two-phase system;

adding 1-bromomethyl-3,5,7-trinitro-1,3,5,7-tetrazacyclooctane to said lower layer contining acetyl azide in methylene chloride;

reacting under non-basic conditions said acetyl azide with said 1-bromomethyl-3,5,7-trinitro-1,3,5,7-tetrazacycloctane at between about 10° and 15° C. to generate 1-azidomethyl-3,5,7-trinitro-1,3,5,7-tetrazacyclooctane; and collecting the final purified 1-azidomethyl-3,5,7-trinitro-1,3,5,7-tetrazacyclooctane.

9. A chemical compound denoted as 1-azidomethyl-3,5,7-trinitro-1,3,5,7-tetrazacyclooctane.

* * * * *